(12) United States Patent
Van Langenhove (10) Patent No.: US 10,694,963 B2
(45) Date of Patent: Jun. 30, 2020

(54) COMPUTER-IMPLEMENTED METHOD FOR IDENTIFYING ZONES OF STASIS AND STENOSIS IN BLOOD VESSELS

(71) Applicant: CORONARY TECHNOLOGIES SARL, Fentange (LU)

(72) Inventor: Glenn Van Langenhove, Merelbeke (BE)

( * ) Notice: Subject to any disclaimer, the term of this patent is extended or adjusted under 35 U.S.C. 154(b) by 203 days.

(21) Appl. No.: 15/570,056

(22) PCT Filed: Apr. 27, 2016

(86) PCT No.: PCT/EP2016/059407
§ 371 (c)(1),
(2) Date: Oct. 27, 2017

(87) PCT Pub. No.: WO2016/174090
PCT Pub. Date: Nov. 3, 2016

(65) Prior Publication Data
US 2018/0116533 A1    May 3, 2018

(30) Foreign Application Priority Data
Apr. 27, 2015   (EP) ..................................... 15165235

(51) Int. Cl.
*G06T 7/00*         (2017.01)
*A61B 6/00*         (2006.01)
(Continued)

(52) U.S. Cl.
CPC ............ *A61B 5/0275* (2013.01); *A61B 6/463* (2013.01); *A61B 6/481* (2013.01); *A61B 6/486* (2013.01);
(Continued)

(58) Field of Classification Search
CPC ....... A61B 5/0275; A61B 6/463; A61B 6/481; A61B 6/486; A61B 6/487; A61B 6/504;
(Continued)

(56) References Cited

U.S. PATENT DOCUMENTS

2011/0306868 A1\* 12/2011 Nagao ................ A61B 5/02007
600/410
2013/0028494 A1\* 1/2013 Groth .................... G06T 7/0012
382/130

(Continued)

FOREIGN PATENT DOCUMENTS

| WO | WO-02/022011 A1 | 3/2002 |
|----|-----------------|--------|
| WO | WO-2010/018500 A1 | 2/2010 |
| WO | WO2010/018500 A2 \* | 2/2010 |

OTHER PUBLICATIONS

International Search Report and Written Opinion dated Sep. 23, 2016 for International Application No. PCT/EP2016/059407, van Langenhove, "Computer-Implemented Method for Identifying Zones of Stasis and Stenosis in Blood Vessels," filed Apr. 27, 2016 (11 pages).

*Primary Examiner* — Ping Y Hsieh
(74) *Attorney, Agent, or Firm* — Clark & Elbing LLP; Susan M. Michaud (57) ABSTRACT

In a first aspect, the current invention concerns a computer-implemented method, system and computer program product for identifying a zone in a blood vessel system with a risk level for stasis, comprising the following steps: a) providing an angiogram of a blood vessel system, said angiogram comprising a time series of images of said blood vessel system, at least some of said images showing a contrast agent present in said blood vessel system; b) identifying at least one zone within said blood vessel system on a multitude of images of said time series; c) characterising variations in greyscale intensity in said zone across at least part (Continued)

of said time series of images; d) characterising an outflow of said contrast agent from said zone on the basis of said variations in intensity in said zone; and e) providing a local risk level for stasis in said zone. In further aspects, the current invention also concerns a computer-implemented method, system and computer program product for identifying a zone in a blood vessel with a risk level for stenosis and stent malpositioning, and for measuring the coronary flow reserve (CFR).

20 Claims, 2 Drawing Sheets (51) Int. Cl.
*A61B 5/0275* (2006.01)
*G16H 50/30* (2018.01)
*G06F 19/00* (2018.01)

(52) U.S. Cl.
CPC .............. *A61B 6/487* (2013.01); *A61B 6/504* (2013.01); *A61B 6/507* (2013.01); *A61B 6/5217* (2013.01); *A61B 6/5235* (2013.01); *G06F 19/00* (2013.01); *G06T 7/0016* (2013.01); *G16H 50/30* (2018.01); *G06T 2207/10076* (2013.01); *G06T 2207/30104* (2013.01)

(58) Field of Classification Search
CPC ..... A61B 6/507; A61B 6/5217; A61B 6/5235; G06H 50/30; G06F 19/00; G06T 7/0016; G06T 2207/10076; G06T 2207/30104
See application file for complete search history.

(56) References Cited

U.S. PATENT DOCUMENTS

2016/0203288 A1* 7/2016 Meng .................. G06T 7/0014
703/2
2016/0278725 A1* 9/2016 Van Nijnatten ........ A61B 6/481

* cited by examiner

COMPUTER-IMPLEMENTED METHOD FOR IDENTIFYING ZONES OF STASIS AND STENOSIS IN BLOOD VESSELS

TECHNICAL FIELD

The invention pertains to the technical field of the analysis of angiograms. This invention contributes to an improved automated identification of zones of stasis and/or stenosis in blood vessel systems.

BACKGROUND

Currently there still exists a high rate of incidence of heart attacks. Angiography, as classically performed by interventional cardiologists or radiologists using a catheter-based, minimally invasive technique, is based on acquiring images of arteries. Using a contrast dye or agent as a mimicking substance for blood, images depicting flow can thus be recorded and physicians may base their diagnosis and subsequently their therapy upon these data. A coronary angiogram is indeed a useful imaging technique but it cannot predict heart attacks well enough. Techniques that can provide more information are invasive, more expensive or have an unproven benefit, e.g. thermography, virtual histology, intravascular ultrasound (IVUS), fractional flow reserve (FFR), palpography, etc. Coronary angiograms contain more information than currently is being used, since it is mostly used to diagnose the severity of stenosis (i.e. abnormal narrowing in a blood vessel). Above 70% stenosis, a percutaneous coronary intervention (PCI) is usually performed on the patient. Below 70% stenosis, first extra info would be welcome. The flow information from angiograms is generally not used at all, while the medical literature has extensively shown that regions of slow flow, regions of altered shear stress, and zones of prolonged contrast agent stasis may account for development of atherosclerotic plaque, rapid progression of atherosclerosis into vulnerable plaque, occurrence of thrombosis and subsequent myocardial infarction, and underdeployment of stents (potentially causing detrimental events such as acute or subacute stent thrombosis). Currently, there are no possibilities to quantify the shear stress in a zone of a blood vessel system in order to provide a risk level of stasis in that zone.

Additionally, the assessment of angiograms is typically paired with a reasonably high level of subjectivity, despite the obvious skills of an aptly trained physician. It is therefore desirable to overcome this problem via a computer application that allows for an objective analysis of angiograms, and more specifically a correct identification of zones of stasis.

Document US 2013-0237815 A1 (D1) discloses a method for determining a four-dimensional angiography dataset describing the flow of contrast agent over time through a blood vessel system of the body of a patient. The four-dimensional flow information is obtained from two-dimensional images captured in a time period in different projection directions using a biplanar x-ray device in an inflow phase and/or an outflow phase of the contrast agent by back projection of the images. The document further discloses that it is conceivable to "automatically undertake a quantitative evaluation of the four-dimensional angiography dataset, for example with regard to flow rates through individual vessels or vessel sections of the vascular system and the like. Such automatic evaluation operations, for example with regard to the cerebral blood flow, are fundamentally already known in the prior art but in the context of the present application can also be carried out on the basis of a dimensional angiography dataset describing the variation with time in high resolution in the three-dimensional space.".

Document US 2013-0253895 A1 (D2) discloses a system and method for quantifying absolute blood volume flow rates by fitting a kinetic model incorporating blood volume, bolus dispersion and signal attenuation to dynamic angiographic data. The method involves acquiring and fitting dynamic angiographic data to a kinetic model to derive parameter maps. A calibration factor is determined using angiographic data to convert the relative blood volume to an absolute blood volume. The parameter maps are used to simulate the expected signal that arises from a bolus of labelled blood with a short duration relative to the dispersion of the bolus in absence of signal decay. The simulated signals are added and converted into the absolute blood volume. An absolute blood volume flow rate within a vessel mask is determined from blood volume and bolus duration. Using this method, time of arrival of the contrast agent to one or more blood vessels can be compared to each other and to a simulated time of arrival in order to assess a level of stenosis.

Document US 2013-0345559 A1 (D3) discloses a quantitative perfusion analysing method which involves injecting a contrast agent into one or more vascular vessels. A set of angiography images is obtained in a time series and associated with flow of the contrast agent in one or more vascular vessels. The time of arrival of the contrast agent is calculated at each selected location associated with the vascular vessels to present the time of arrival to a user.

Document WO 2010/018500 A1 (D4) discloses a method for dynamically visualizing coronary information and an apparatus adapted to implement such method. In a preferred embodiment of the method, first dynamic cardiac data is acquired during a first cardiac stage and second dynamic cardiac data is acquired during a second cardiac stage. Then, the two data sets are visualized continuously in a superimposed presentation, wherein the first cardiac data and the second cardiac data corresponding to a same phase within the cardiac cycle are visualized simultaneously. In this way for example information about the vessel geometry may be immediately linked with information about the muscle irrigation or perfusion. Furthermore, this information may be displayed in a high-contrasted and low-noise presentation.

Document WO 02/22011 A1 (D5) discloses a method for pictorially depicting and diagnosing thrombi and to the use of particle suspensions for producing contrast agents for depicting thrombin by means of nuclear spin tomography.

There remains a need in the art for an improved identification and diagnose of zones of stasis in blood vessel systems, more in particular for coronary blood vessel systems. The present invention aims to resolve at least some of the problems mentioned above. The invention thereto aims to provide a computer-implemented method for identifying zones of stasis in blood vessels, in order to prevent coronary obstructions from happening.

SUMMARY OF THE INVENTION

In a first aspect, the present invention provides a computer-implemented method, system and computer program product for identifying a zone in a blood vessel system with a risk level for stasis, comprising the following steps:

a) providing an angiogram of a blood vessel system, said angiogram comprising a time series of images of said blood vessel system, at least some of said images showing a contrast agent present in said blood vessel system;

b) identifying at least one zone within said blood vessel system on a multitude of images of said time series;

c) characterising variations in greyscale intensity in said zone across at least part of said time series of images;

d) characterising an outflow of said contrast agent from said zone on the basis of said variations in intensity in said zone;

e) providing a local risk level for stasis in said zone, taking into account the outflow characteristics of said contrast agent from said zone.

The abovementioned D1, D2 and D3 do not seem to disclose that characteristics of the outflow of contrast agent can be used to provide a risk level for stasis for a specific zone in the blood vessel system, by comparing the outflow characteristics for said specific zone to the outflow characteristics of other zones of the same blood vessel system. The present invention improves on the state of the art by automating the analysis of a coronary angiogram and by being able to provide an indication of the risk level for stasis in the blood vessel system. The inventors have surprisingly found that outflow characteristics for a zone in a vessel are particularly indicative of zones of stasis, in particular the flow rate at which a contrast agent flows out of the zones has been observed as a highly differentiating characteristic.

Also D4 or D5 do not disclose that the outflow of the contrast agent from a zone is characterized, thereby allowing to obtain an improved risk level assessment for stasis in that zone. Hereby it can be noted that the outflow of the contrast agent refers to the end of the bolus of the contrast agent. I.e. in order to obtain an angiograph, an amount of contrast agent is injected in the vascular system. This amount of contrast agent forms at least one bolus which can be tracked. A bolus has a beginning and an end, which can be seen in an angiograph as clear changes in intensity level. When a bolus enters a zone, the intensity changes (typically decreases) drastically. Also when a bolus leaves a zone, the intensity changes (typically increases) drastically. The present invention basically focusses on the way the bolus leaves a zone, i.e. on the way the contrast agent flows out of such a zone. Hereby, the inventors have found that by characterizing how the contrast agent flows out the zone, a risk level for stasis in that zone can be obtained more precise and in an automated or semi-automated way.

In a second aspect, the present invention provides a system suitable for identifying a zone in a blood vessel system with a risk level for stasis, which comprises a processing unit configured for the execution of the computer-implemented method as described above.

In a third aspect, the present invention provides a computer program product suitable for identifying a zone in a blood vessel system with a risk level for stasis, which comprises at least one computer-accessible medium, on which computer-accessible program code portions are saved, which comprise instructions for the execution of the computer-implemented method as described above.

In further aspects, the current invention also concerns a computer-implemented method, system and computer program product for identifying a zone in a blood vessel with a risk level for stenosis and stent malpositioning, and for measuring the coronary flow reserve (CFR).

Further preferred embodiments are described in the claims and further in this document.

DESCRIPTION OF FIGURES

The invention is further described by the following non-limiting figures which illustrate part of the invention, and are not intended to, nor should they be interpreted to, limit the scope of the invention.

FIG. 2 shows a normal case, where the sudden increase in intensity indicates a quick contrast agent outflow.

FIG. 3 shows a problem case, where the increase occurs more gradually, meaning a slower contrast agent outflow.

DETAILED DESCRIPTION OF THE INVENTION

Unless otherwise defined, all terms used in disclosing the invention, including technical and scientific terms, have the meaning as commonly understood by one of ordinary skill in the art to which this invention belongs.

As used herein, the following terms have the following meanings:

"A", "an", "the" and "said" as used herein refers to both singular and plural referents unless the context clearly dictates otherwise. By way of example, "a compartment" refers to one or more than one compartment.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

In a first aspect, the invention provides a computer-implemented method for identifying a zone in a blood vessel system with a risk level for stasis, according to claim 1.

In a preferred embodiment of the invention, said identification of at least one zone within said blood vessel system on a multitude of images of said time series (step b) is performed by detecting the blood vessels that are filled with contrast agent (referred to as "segmentation"), from which the edges of said zone can additionally be derived, and optionally by extrapolating a position of said zone from images showing said contrast agent in or near said zone to images not showing said contrast agent near or in said zone, thereby identifying said zone across said multitude of images (referred to as "point tracking"). Said segmentation and point tracking steps are provided to detect the main arterial branches of interest across said multitude of images, respectively to provide a sufficient amount of correct points suitable for relevant contrast agent intensity monitoring (see further below).

In a preferred embodiment of the invention, said characterisation of variations in intensity in said zone across at least part of said time series of images (step c; referred to as "intensity monitoring") comprises variations in intensity which are indicative of contrast agent flow in and/or through said zone. Said intensity monitoring uses the result of the point tracking as the correct positions around which to monitor the intensity, and for this region of interest the mean pixel intensity is computed. See FIGS. 2-3 for examples of curve fitting on said intensity variation data.

In a preferred embodiment of the invention, said characterisation of outflow of contrast agent from said zone on the basis of said variations in intensity in said zone (step d) is performed by computing an outflow rate of said contrast agent from said zone, optionally by computing a rate of intensity variation in said zone on said images. The assessment of said zones of altered flow in said vessels, more specifically in coronary arteries, has the advantage of better identifying the treatment focus.

Figure 2:
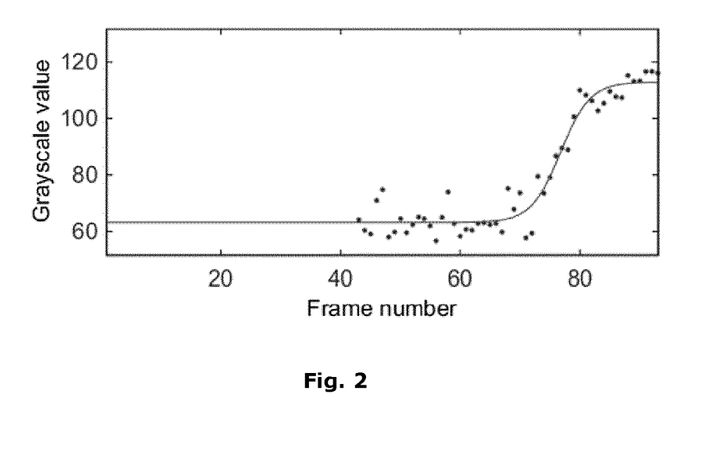
FIGS. 2-3 shows examples of sigmoid curve fitting on contrast agent intensity variations (Y-axis) over a time period (X-axis) for two different selected points in coronary arteries.
Figure 3:
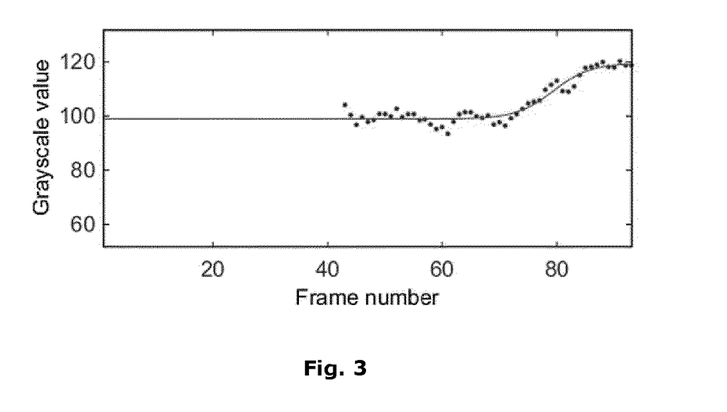

A characterization of the outflow can be illustrated using FIGS. 2 and 3. In FIG. 2, for instance, the outflow of the contrast agent occurs between frame numbers 65 and 85, whereby the intensity increases from about 64 to about 112. By fitting the intensity datapoints to a curve, e.g. a sigmoid curve, a maximal slope can be obtained for the intensity variation, this maximal slope characterizing the rate at which the contrast agent leaves the zone, i.e. the outflow rate. Another characteristic which can be obtained is the time needed for the intensity to increase from e.g. 10% to 90% of the variation. For FIG. 2 in particular, this means the number of frames needed for the intensity to increase from 68.8 (=64+10%×(112−64)) to 107.2 (=64+90%×(112−64)), which is around 11 frames. This characteristic relates to a weighted average rate of outflow of contrast agent. Similar characterizations can be performed for FIG. 3, where the contrast agent flows out of the zone about frame numbers 68 and 89, thereby increasing from almost 100 to almost 120.

In a preferred embodiment of the invention, said provision of a local risk level for stasis in said zone (step e) is performed by comparing said outflow characteristics of said zone to corresponding outflow characteristics of one or more other zones of said blood vessel system. This allows the identification of zones with a high likelihood of plaque development, and thus potentially a more targeted treatment approach, additionally the imaging of plaques prone to rupture (with a likelihood of causing a myocardial infarction) and finally the identification of incomplete apposition of stents (and by better expanding these stents, reducing the risk of acute or sub-acute thrombosis). Furthermore, by comparing outflow characteristics of a zone with corresponding outflow characteristics of other zones in the same angiogram, it is possible to make a comparison which is independent of altered circumstances across different angiogram recordings. Indeed, whereas it is possible to compare outflow characteristics of a zone in a first angiogram to the outflow characteristics of the same zone in a second angiogram, it remains difficult to compensate for the differences between the two angiograms which originate from altered circumstances such as differing angiogram recording apparatus, differing angiogram recording apparatus settings, a different state of the person (e.g. well-rested vs. tired, different hormonal balance), etc.

In a preferred embodiment of the invention, said corresponding outflow characteristics of the one or more other zones of said blood vessel system are obtained performing the steps (a)-(d) for each of said one or more other zones, and more preferably, the method also comprises the step (e) of providing said local risk level for stasis for each of said one or more other zones, taking into account the outflow characteristics of said contrast agent from said one or more other zones respectively.

In a preferred embodiment of the invention, said blood vessel system comprises one or more coronary arteries.

In a preferred embodiment of the invention, said comparison of said outflow characteristics of said zone to outflow characteristics of said one or more other zones comprises a comparison of a rate of intensity variation and/or a comparison of a moment in time at which an intensity variation in said zone and said one or more other zones has occurred.

Figure 4:
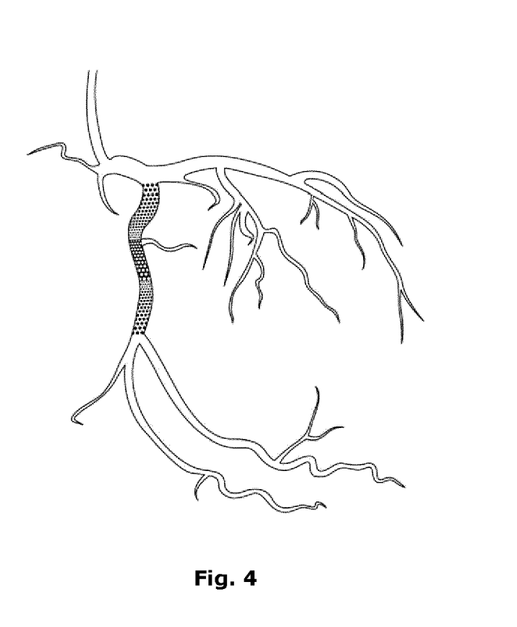
FIG. 4 shows an image of coronary arteries with hatched patterns indicating the presence of abnormal blood flow patterns, based upon the characteristics of the intensity variations over time (slope, shift, etc.).

In a preferred embodiment of the invention, said zones of increased risk for stasis are automatically and quantifiably identified in relation to a standardized risk level scale, and preferably also in relation to one or more risk level thresholds. For example, FIG. 4 shows an image of coronary arteries with hatched patterns indicating the presence of abnormal blood flow patterns, based upon the characteristics of the intensity variations over time. Since stasis could lead to embolism, said quantification allows to better decide whether a treatment or a surgical procedure is necessary, as well as at which of said zones a possible surgical treatment should be performed, optionally said treatment or procedure being pro-active.

In a preferred embodiment of the invention, a global risk level for stasis of said blood vessel system is obtained taking into account the local risk levels of one or more zones in the blood vessel system. Whereas local risk levels are derived from specific positions of altered blood flow, combined they result in said global risk level, which indicates whether a patient in general is at risk of developing any of the mentioned medical disorders.

In a preferred embodiment, said computer-implemented method comprises a learning phase using the input of one or more skilled physicians, who assess a large number of angiograms for risk levels, which can be correlated to said computed outflow characteristics, thereby obtaining an objective calibration scale for both local risk level and global risk level. For instance, a skilled physician is shown e.g. 100 angiograms, and is asked to give a score on a standardized risk level scale from e.g. 1 to 10, where "1" means no identifiable global risk for a medical disorder and "10" means immediate surgical intervention. If the global risk level is different from 1, the physician is further asked to identify the zones in the blood vessel system on the basis of which he or she has made the assessment as well as an indication of the risk for stasis in that zone, e.g. by giving a local score on a scale from 1 (meaning a slight possibility for stasis) to 10 (meaning a near certainty of stasis and warranting immediate surgery on the basis of that zone by itself). By comparing the assessed global and local scores to the risk levels which are computed taking into account the outflow characteristics of contrast agent from the indicated and other, non-indicated, zones of the blood vessel system, important thresholds for both local and global risk levels can be identified in an objective manner. Such a learning phase thus allows to obtain objective thresholds for local and global risk levels as obtained in a method according to the present invention.

In a preferred embodiment of the invention, said blood vessel system of a patient is monitored by taking said angiograms at specific instances (e.g., every three months, depending on the condition of said patient), to identify the following:

i. said local risk level of said zone of stasis and its variation across different angiograms;
ii. said global risk level for stasis of said blood vessel system and its variation in time.

In a preferred embodiment, said angiogram comprises a time series of three-dimensional images. In this case, one can refer to the angiogram as a 4D-angiogram. The three-dimensional images can be reconstructed from two-dimensional images captured in a time period in different projection directions using a biplanar x-ray device, e.g. as disclosed in US 2013-0237815 A1, or by any other method.

In a second aspect, the invention provides a system suitable for identifying a zone in a blood vessel system with a risk level for stasis, which comprises a processing unit configured for the execution of the computer-implemented method as described above.

In a third aspect, the invention provides a computer program product suitable for identifying a zone in a blood vessel system with a risk level for stasis, which comprises at least one computer-accessible medium, on which computer-accessible program code portions are saved, which comprise instructions for the execution of the computer-implemented method as described above.

It is supposed that the present invention is not restricted to any form of realization described previously and that some modifications can be added to the presented example of fabrication. For example, the present invention has been described referring to contrast agent outflow characteristics from intensity variations, but it is clear that the invention, or parts of the invention, have a high potential to be applied to obtain other, additional features, for instance: blood flow velocity mapping, an indication of the quality of an acute stent implementation, automatic detection of stenosis and/or a non-invasive measurement of the coronary flow reserve (CFR).

Hence, in an embodiment, the present invention provides for a method which automatically detects stent malpositioning, which is characterised by an amount of blood or contrast agent remaining between the stent and the vessel wall, and/or by a period for which blood or contrast agent remains between the stent and the vessel wall. Both amount and period can be computed by a similar method as stasis detection, e.g. by taking into account outflow characteristics of the contrast agent.

Hence, in another embodiment, the present invention provides a non-invasive measurement of the coronary flow reserve (CFR; the maximum increase in blood flow through the coronary arteries above the normal resting volume) by using angiogram movies or images in order to compare baseline blood velocities with blood velocities after a vessel-widening adenosine injection, whereby preferably the location of the contrast agent at a certain time is determined by outflow characteristics of the contrast agent.

For example, the contrast agent velocity between two points A and B along a vessel segment of interest, can be calculated by dividing the distance between points A and B ($\Delta x$) by the difference in time between the occurrences of 90% of the maximally observed contrast agent intensity in point A ($T_A$, i.e. a short while before the contrast agent has passed point A completely), compared to that in point B ($T_B$):

$$V = \frac{\Delta x}{T_B - T_A}$$

This method, or similar formulas, can then be used to determine and compare flow velocities across different angiograms.

In a further aspect, the present invention provides for an indication whether or not to surgically intervene, based on various indications (e.g., stasis, stenosis, stent malpositioning, CFR, or any combination thereof), which together result in a better evaluation than it was attainable up to this moment.

Therefore, in an aspect, the present invention provides for an indication whether or not to surgically intervene, based on various indications (e.g., stasis, stenosis, stent malpositioning, CFR, or any combination thereof), which together result in a better evaluation than it was attainable up to this moment.

The invention is further described by the following non-limiting examples which further illustrate the invention, and is not intended to, nor should it be interpreted to, limit the scope of the invention.

Example 1

Figure 1:
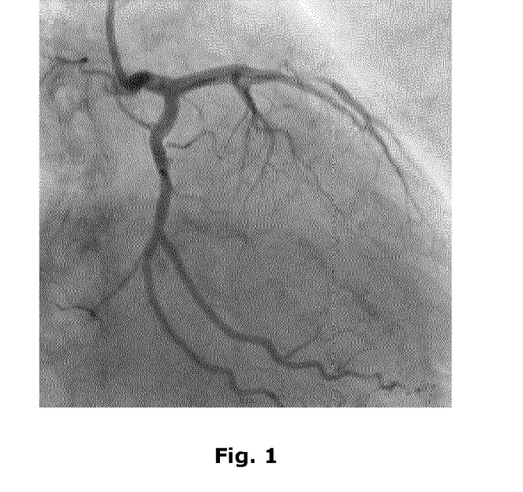
FIG. 1 shows a still frame of coronary arteries taken from a typical angiogram.

In an embodiment, the present computer-implemented method for identifying a zone in a blood vessel system with a risk level for stasis comprises the following steps:

a) Data Sourcing:

An angiogram movie consisting of multiple frames (e.g., FIG. 1) is provided in a DICOM (Digital Imaging and Communications in Medicine) format, and is imported and converted to a file format usable for processing by MAT-LAB®.

b) Background Elimination:

In order to obtain the artery (=foreground) as it would appear without the background in the image, the background is subtracted from the original image. This involves estimating the background of each frame based on the maximal intensity value for each pixel in a time window around this frame. The highest intensity at each position is assumed to be the background intensity and is subtracted from the original image. Background suppression may result in a better artery segmentation (see below), due to the removal of background structures and artefacts (e.g., due to the patient's respiration or motion of the support table).

c) Artery Segmentation:

To separate the artery from the background image, each frame is processed separately. First, the contrast of the image is enhanced by stretching the histogram of the pixel intensity values. Second, vessel structures in the image are enhanced by assigning an intensity value to each pixel, based on its likeness to appear in a vessel ('vesselness'). The more a pixel is likely to be part of a vessel, the higher the intensity value will be. Third, only the pixels having a certain intensity as a measure of 'vesselness' will be kept ('thresholding'). This removes the pixels unlikely to be part of a vessel from the object. Last, small objects unattached to the main arteries (noise) are removed.

d) Mask Application:

In the original image, only the pixels which are part of the segmented arteries are kept. All other pixels are set to zero.

e) Skeleton Operations:

In some embodiments of the invention, the 'skeleton' of the arteries is computed, first the segmented arteries are reduced to a width of one pixel and small loose parts are removed. Second, characteristic points of arteries that can be used for tracking (=branch points and endpoints) are computed. Last, unconnected parts of the skeleton are linked by tracing a line on the image between these points.

f) Segment Tracking:

The selection of relevant vessel points of a zone in the blood vessel system can either be performed manually, e.g. by clicking on the image, or automatically, e.g. by locating junctions. Point tracking can either be based on (a) its position, by choosing a junction or endpoint, looking for the closest junction or endpoint in the next frame, and updating the position for the next frame, or (b) template matching, by defining a template as a small region around the selected point in the original image, looking for the position with the highest correlation to the template in the next image, and updating the template for matching in the next frame. Template matching is restricted to positions in the segmentation mask, to avoid having points matched on artefacts or background structures. If needed, the tracking is corrected by selecting the correct position and updating the template matching.

After point tracking, the tracked points are connected along the artery. This connection is performed by computing a grey level distance transform in each frame, starting from one of the points to connect. This distance transform takes both distance and difference in greyscale intensity into account to compute the 'cost' of each path connecting both points. The path with the lowest cost is selected. An incorrect path can be corrected by inserting a penalty to a wrong region of the path and re-computing the path with the lowest cost. Connecting the points using (the shortest path along) the skeleton is an alternative to this method.

Once the path has been computed and thus a segment has been tracked, a user-defined number of points are placed along the segment in each frame. Using a certain size, shape and mask, a region of interest (ROI) is defined around each of these points for intensity monitoring (see below).

g) Intensity Monitoring

This step uses the result of the segment tracking and the previously defined points along the segment as the positions around which to monitor the greyscale intensity. For each of the defined ROI's the mean pixel intensity in their zone is computed. The pixels used for intensity monitoring around each point have to be part of both the ROI and the segmentation mask. A point within the ROI but not in the segmentation mask, and thus part of the background, is not included when computing the mean intensity around a point.

h) Presentation of the Results

To present the output of the intensity monitoring in a way that is both clear and helpful to the user, three methods are proposed:

i. To analyse the outflow in each of the points, a sigmoid curve is fitted to the intensity data (e.g., FIGS. 2-3). A number of characteristics for the outflow of contrast agent can be extracted from the sigmoid equation resulting from the curve fitting. Examples of parameters are the intensity change, the time required for outflow and the slope of the curve. The goodness of fit of the curve fitting can also be used to detect points where noise in the intensity data makes correct fitting impossible. Points with a bad goodness of fit are not analyzed further because the parameters cannot be trusted to correctly represent the outflow of the contrast agent. The sigmoid equation used for the curve fitting is the following:

$$y = \frac{t-b}{1+\exp(s*(x_0-x))} + b$$

where t is the maximal value of the sigmoid, b its minimal value, x0 the coordinate of the inflection point of the sigmoid and s a measure for the steepness of the curve. The start and the end of the outflow can be detected as the maximum and minimum of the second derivative of the curve, respectively. The time between these points represents the time required for the contrast agent to flow out at this position in the artery. This time value, together with the difference between the minimal and the maximal intensity values, can be used to compute the average slope of the curve during outflow.

ii. Plotting time series of the intensity variations in several zones along a selected segment of the arteries.

iii. Presenting an image of the arteries with hatched patterns or a colour map (e.g., FIG. 4) indicating the presence of abnormal blood flow patterns, based upon the characteristics of the intensity variations over time (slope, shift, etc.).

i) Providing a Risk Level for Stasis

A risk level for stasis is provided based on the curve's slope, shift and other characteristics, which are compared for several zones or regions of interest. The determination of said risk level can for example be obtained by comparing the present results with reference angiograms of actual risk situations (e.g., angiograms taken after the incidence of a heart attack) or with reference thresholds obtained from feedback from an experienced practitioner. Thus, hereby critical thresholds of the abovementioned characteristics are proposed, based on whether or not zones of stasis are encountered.

Overall, this method allows to better decide whether a treatment or a surgical procedure is necessary, as well as at which of said zones a possible surgical treatment should be performed, optionally said treatment or procedure being pro-active. For example, using the present embodiment of the invention, a first region of interest 'A' might be catalogued as potentially dangerous with respect to stasis, whereas after further visual assessment by a physician it could be declared harmless. Contrarily, a physician might not have noticed the genuine danger in another region of interest 'B', whereas the invention does properly indicate the risk level for stasis.

Example 2

In an embodiment, the present computer-implemented method is applied for the detection of stenosis, using the steps (a)-(c) of claim 1 and with the subsequent addition of steps comprising:

d1) Serving as inputs for the computer-implemented method, are:
i. a blood vessel segment selected by the user
ii. a segmentation mask e1) For each point in the segment, the radius of the vessel is computed, as well as the stenosis percentage based on its neighbouring points f1) Presentation of the results comprise a diagram whereby points above a certain stenosis percentage are indicated. For example, the stenosis percentage can be divided in the following classes: <30%, 30-50, 50-70, 70-95% and >95%. Optionally, the diagram can be accompanied with a warning should some points' percentages lie above a given percentage. These points will then also be indicated (e.g., using a specific colour) in one or more of the used angiogram images.

Overall, this method allows to better decide whether a treatment or a surgical procedure is necessary, as well as at which of said zones a possible surgical treatment should be performed, optionally said treatment or procedure being pro-active.

The invention claimed is:

1. Computer-implemented method for identifying a zone in a blood vessel system with a risk level for stasis, comprising the following steps:
   a) providing an angiogram of a blood vessel system, said angiogram comprising a time series of images of said blood vessel system, at least some of said images showing a contrast agent present in said blood vessel system;
   b) identifying at least one zone within said blood vessel system on a multitude of images of said time series;
   c) characterising variations in greyscale intensity in said zone across at least part of said time series of images, wherein the variations in greyscale intensity are indicative of contrast agent flow in and/or through said zone;
   d) characterising an outflow of said contrast agent from said zone on the basis of said variations in intensity in said zone;
   e) providing a local risk level for stasis in said zone, wherein the zones of increased risk for stasis are automatically and quantifiably identified in relation to a standardized risk level scale, taking into account the outflow characteristics of said contrast agent from said zone.

2. Method according to claim 1, characterised in that said identification of at least one zone within said blood vessel system on a multitude of images of said time series is obtained by detecting blood vessels that are filled with contrast agent, from which the edges of said zone can additionally be derived, and optionally extrapolating a position of said zone from images showing said contrast agent in or near said zone to images not showing said contrast agent near or in said zone, thereby identifying said zone across said multitude of images.

3. Method according to claim 1, characterised in that said risk level for stasis in said zone is obtained by comparing said outflow characteristics of said zone to corresponding outflow characteristics of one or more other zones of said blood vessel system.

4. Method according to claim 3, characterised in that said comparison of said outflow characteristics of said zone to outflow characteristics of said one or more other zones comprises a comparison of a rate of intensity variation.

5. Method according to claim 3, wherein said comparison of said outflow characteristics of said zone to outflow characteristics of said one or more other zones additionally comprises a comparison of a moment in time at which an intensity variation in said zone and said one or more other zones has occurred.

6. Method according to claim 3, characterised in that said corresponding outflow characteristics of the one or more other zones of said blood vessel system are obtained performing the steps (a)-(d) of claim 1 for each of said one or more other zones, and more preferably, method also performing the step (e) of providing said local risk level for stasis for each of said one or more other zones, taking into account the outflow characteristics of said contrast agent from said one or more other zones.

7. Method according to claim 1, characterised in that said blood vessel system comprises one or more coronary arteries.

8. Method according to claim 1, characterised in that a global risk level for stasis of said blood vessel system is obtained, taking into account said local risk levels for stasis in said one of more zones within said blood vessel system.

9. Method according to claim 1, characterised in that the blood vessel system of a patient is monitored by taking said angiograms at specific instances, to identify the following:
   i) said local risk level of said zone of stasis and its variation across different angiograms;
   ii) said global risk level for stasis of said blood vessel system and its variation in time.

10. Method according to claim 1, characterised in that the steps (a)-(c) of claim 1 are applied for the detection of stenosis, with the subsequent addition of steps comprising:
    d1) providing a blood vessel segment selected by the user and a segmentation mask as inputs for the computer-implemented method;
    e1) computing the radius of the blood vessel for each point in the segment, as well as the stenosis percentage based on its neighbouring points;
    f1) presenting the results whereby points above a certain stenosis percentage are indicated.

11. Method for indicating a degree of necessity of a surgical intervention comprising identifying a zone in a blood vessel system with a risk level for stenosis according to a method as in claim 10.

12. Method according to claim 1, whereby the steps (a)-(d) of claim 1 are applied for the detection of stent malpositioning, with the subsequent addition of steps comprising:
    e1) providing a local risk level for stent malpositioning in said zone, taking into account the outflow characteristics of said contrast agent from said zone.

13. Method for indicating a degree of necessity of a surgical intervention comprising identifying stent malpositioning according to a method as in claim 12.

14. Method according to claim 1, whereby the steps (a)-(d) of claim 1 are applied for the non-invasive measurement of the coronary flow reserve (CFR), with the subsequent addition of steps comprising:
    e1) computing the contrast agent velocity between two points A and B along a blood vessel segment, taking into account the outflow characteristics of said contrast agent at said points.

15. System suitable for identifying a zone in a blood vessel system with a risk level for stasis, stenosis and/or stent malpositioning and for measuring the coronary flow reserve (CFR), which comprises a processing unit configured for the execution of the computer-implemented method according to claim 1.

16. Computer program product suitable for identifying a zone in a blood vessel system with a risk level for stasis, stenosis and/or stent malpositioning and for measuring the coronary flow reserve (CFR), which comprises at least one computer-accessible medium, on which computer-accessible program code portions are saved, which comprise instructions for the execution of the computer-implemented method according to claim 1.

17. Method for indicating a degree of necessity of a surgical intervention comprising identifying zones of stasis according to a method as in claim 1.

18. Method according to claim 1, wherein step c) comprises the step of fitting a curve to a time sequence of intensity datapoints, and wherein step d) comprises the step of obtaining one or more characteristics of the outflow of said contrast agent from the fitted curve.

19. Method according to claim 18, wherein said curve is a sigmoid curve.

20. Method according to claim 18, wherein said one or more outflow characteristics comprise an intensity change, a time required for outflow and/or a slope of the curve.

\* \* \* \* \*